(12) United States Patent
Schuster (10) Patent No.: US 9,393,077 B2
(45) Date of Patent: Jul. 19, 2016

(54) MEDICAL STERILE CONTAINER AND METHOD FOR DETERMINING THE STERILIZATION STATUS OF A MEDICAL STERILE CONTAINER

(71) Applicant: Aesculap AG, Tuttlingen (DE)

(72) Inventor: Stefan Schuster, Villingen-Schwenningen (DE)

(73) Assignee: Aesculap AG, Tuttlingen (DE)

( * ) Notice: Subject to any disclaimer, the term of this patent is extended or adjusted under 35 U.S.C. 154(b) by 231 days.

(21) Appl. No.: 14/225,545

(22) Filed: Mar. 26, 2014

(65) Prior Publication Data

US 2014/0224687 A1 Aug. 14, 2014

Related U.S. Application Data

(63) Continuation of application No. PCT/EP2012/070944, filed on Oct. 23, 2012.

(30) Foreign Application Priority Data

Oct. 26, 2011 (DE) .......................... 10 2011 054 827

(51) Int. Cl.
*A61B 19/00* (2006.01)
*A61L 2/26* (2006.01)
*A61L 2/28* (2006.01)

(52) U.S. Cl.
CPC . *A61B 19/38* (2013.01); *A61L 2/26* (2013.01); *A61L 2/28* (2013.01); *A61B 2090/081* (2016.02); *A61L 2202/182* (2013.01)

(58) Field of Classification Search
CPC ............. A61L 2/26; A61L 2/28; A61B 19/00

USPC ......................................................... 422/292
See application file for complete search history.

(56) References Cited

U.S. PATENT DOCUMENTS

| | | | |
|---|---|---|---|
| 2,024,004 | A | 12/1935 | Jewell et al. |
| 2,613,130 | A | 10/1952 | Jewell et al. |
| 2,715,251 | A | 8/1955 | Vischer, Jr. |
| 3,034,819 | A | 5/1962 | Tupper |
| 3,484,036 | A | 12/1969 | Meyers |
| 3,924,800 | A | 12/1975 | Desmond et al. |
| 3,972,416 | A | 8/1976 | Underwood |

(Continued)

FOREIGN PATENT DOCUMENTS

| | | |
|---|---|---|
| CN | 1498119 | 5/2004 |
| CN | 1899211 | 1/2007 |

(Continued)

*Primary Examiner* — Sean E Conley
(74) *Attorney, Agent, or Firm* — Lipsitz & McAllister, LLC (57) ABSTRACT

In a first aspect of the invention, a medical sterile container has a container interior for accommodating articles to be sterilized. The medical sterile container comprises a pressure-activatable sterilization status detection device for detecting a sterilization status of the sterile container. In a second aspect of the invention, a method for determining the sterilization status of a medical sterile container having a container interior for accommodating articles to be sterilized is provided. While the sterile container is undergoing a sterilization process in a sterilization apparatus, pressure differences to which the sterile container is thereby subjected are detected, and the sterilization status sterile is allocated to the sterile container if during the sterilization process a limit value for a pressure gradient per time unit is exceeded.

23 Claims, 4 Drawing Sheets

(56) References Cited

U.S. PATENT DOCUMENTS

| | | |
|---|---|---|
| 4,372,921 A | 2/1983 | Sanderson et al. |
| 4,416,417 A | 11/1983 | Sanderson et al. |
| 4,457,327 A | 7/1984 | Pepper |
| 4,509,196 A | 4/1985 | Sak et al. |
| 4,512,498 A | 4/1985 | Leibinger |
| 4,551,311 A | 11/1985 | Lorenz |
| 4,562,047 A | 12/1985 | Sestak et al. |
| 4,625,885 A | 12/1986 | Nichols |
| 4,661,326 A | 4/1987 | Schainholz |
| 4,682,688 A | 7/1987 | Budert |
| 4,782,942 A | 11/1988 | Ashley et al. |
| 4,783,321 A | 11/1988 | Spence |
| 4,820,499 A | 4/1989 | Taschner |
| 4,915,913 A | 4/1990 | Williams et al. |
| 5,176,884 A | 1/1993 | Taschner et al. |
| 5,225,162 A | 7/1993 | Scoville |
| 5,328,661 A | 7/1994 | Taschner |
| 5,346,075 A | 9/1994 | Nichols et al. |
| 5,382,528 A | 1/1995 | Scoville |
| 5,508,006 A | 4/1996 | Gabele et al. |
| 5,524,755 A | 6/1996 | Deeds |
| 5,690,713 A | 11/1997 | Bowerman et al. |
| 6,053,914 A | 4/2000 | Eggers et al. |
| 6,077,485 A | 6/2000 | Baker |
| 6,145,687 A | 11/2000 | Nichols et al. |
| 6,295,330 B1 | 9/2001 | Skog et al. |
| 7,172,740 B2 | 2/2007 | Gleichauf et al. |
| 7,744,832 B2 | 6/2010 | Horacek et al. |
| 2004/0256269 A1 | 12/2004 | Gleichauf et al. |
| 2008/0125624 A1 | 5/2008 | Hatori |
| 2008/0187465 A1 | 8/2008 | Horacek et al. |

FOREIGN PATENT DOCUMENTS

| | | |
|---|---|---|
| DE | 747 432 | 9/1944 |
| DE | 82 13 351 | 10/1982 |
| DE | 31 16 036 | 11/1982 |
| DE | 33 16 141 | 11/1984 |
| DE | 34 38 463 | 4/1986 |
| DE | 35 00 026 | 7/1986 |
| DE | 35 44 341 | 6/1987 |
| DE | 36 32 674 | 4/1988 |
| DE | 198 35 503 | 2/2000 |
| DE | 201 18 910 | 3/2002 |
| DE | 20 2009 010 210 | 11/2009 |
| EP | 0 281 255 | 9/1988 |
| JP | 5441591 | 4/1979 |
| JP | 03222956 | 10/1991 |
| JP | 2000185047 | 7/2000 |
| JP | 2006180935 | 7/2006 |
| JP | 2010516425 | 5/2010 |
| WO | 79/00077 | 2/1979 |
| WO | WO 92/06899 | 4/1992 |
| WO | WO 00/51648 | 9/2000 |

MEDICAL STERILE CONTAINER AND METHOD FOR DETERMINING THE STERILIZATION STATUS OF A MEDICAL STERILE CONTAINER

CROSS-REFERENCE TO RELATED APPLICATIONS

This application is a continuation of international application number PCT/EP2012/070944 filed on Oct. 23, 2012 and claims the benefit of German application number 10 2011 054 827.0 filed on Oct. 26, 2011, which are incorporated herein by reference in their entirety and for all purposes.

FIELD OF THE INVENTION

The present invention relates to medical sterile containers generally, and more specifically to a medical sterile container having a container interior for accommodating articles to be sterilized.

The present invention also relates to methods for determining the sterilization status of a medical sterile container generally, and more specifically to a method for determining the sterilization status of a medical sterile container having a container interior for accommodating articles to be sterilized.

BACKGROUND OF THE INVENTION

Medical sterile containers, also referred to as sterilization containers or sterile containers, are used, in particular, by surgeons and their assistants to sterilize and store surgical instruments and implants in a simple way. For this purpose, the articles to be sterilized, after thorough cleaning, are first placed in the container interior. After closure, the sterile container is sterilized in a sterilization apparatus, also referred to as sterilizer or autoclave, together with its contents. In order that sterilization of the contents of the sterile container is possible at all in the closed state, the latter usually comprises gas exchange openings which allow saturated steam to enter the container interior to sterilize the container contents. The gas exchange openings may be permanently open for gas exchange. In this case, they are then completely closed by a sterile barrier, for example, a filter, but the sterile barrier allows gas exchange. Alternatively, gas exchange openings may also be closed by valves, which only open when the sterile container is located in the sterilization apparatus and is undergoing a sterilization process, in order to allow saturated steam to flow into the container and, possibly, moisture to exit from it again, and automatically close the gas exchange openings again after completion of the process.

In a sterilization process, the sterile container undergoes hot steam treatment in a sterilization apparatus, during which it is subjected to saturated steam at a temperature of typically 134° and a pressure of approximately 3.1 bar for a prescribed duration of between 3 and 60 minutes.

After it has undergone the complete sterilization process in the sterilization apparatus, the sterilization status "sterile" can be allocated to the sterile container, i.e., its interior and the articles contained therein.

In sterile containers available on the market, it is known to automatically set the sterilization status to "sterile" and indicate in a corresponding manner when a limit temperature is exceeded during the sterilization process. For example, optical indicators are known, which, after a temperature of, for example, 115° is exceeded, change their color and, therefore, indicate to a user that the sterile container has allegedly undergone a sterilization cycle.

A disadvantage of such systems is, however, that they only react to temperature changes. In other words, the sterilization status "sterile" would also be allocated to a sterile container if the prescribed temperature had been exceeded, but no saturated steam had flowed into the container for sterilization of the articles contained in the container.

Since the validation of the sterilization process is extremely important, in particular, in hospitals, all kinds of indicators of the sterilization status which allocate the sterilization status "sterile" to a sterile container when there is no clear guarantee that this sterilization status actually exists are unacceptable. Consequently, temperature-activated sterilization status detection is unsuitable for establishing with absolute certainty that the sterile container and its contents have undergone a sterilization process properly.

Therefore, it would be desirable to provide a medical sterile container and a method for determining the sterilization status of a medical sterile container which allow reliably allocating the sterilization status "sterile".

SUMMARY OF THE INVENTION

In a first aspect of the invention, a medical sterile container has a container interior for accommodating articles to be sterilized. The medical sterile container comprises a pressure-activatable sterilization status detection device for detecting a sterilization status of the sterile container.

In a second aspect of the invention, a method for determining the sterilization status of a medical sterile container having a container interior for accommodating articles to be sterilized is provided. While the sterile container is undergoing a sterilization process in a sterilization apparatus, pressure differences to which the sterile container is thereby subjected are detected, and the sterilization status sterile is allocated to the sterile container if during the sterilization process a limit value for a pressure gradient per time unit is exceeded.

BRIEF DESCRIPTION OF THE DRAWING FIGURES

The foregoing summary and the following description may be better understood in conjunction with the drawing figures, of which.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical sterile container having a container interior for accommodating articles to be sterilized, said medical sterile container comprising a pressure-activatable sterilization status detection device for detecting a sterilization status of the sterile container.

Provision of a pressure-activatable sterilization status detection device has the advantage over a temperature-activatable sterilization status detection device that the correct sterilization status can be allocated to a sterile container with practically absolute certainty. The pressure-activatable sterilization status detection device makes it possible, in particular, to use pressure changes during performance of a sterilization process and to conclude from these that such a sterilization process has been performed properly. In particular, after the actual sterilization with hot steam under high pressure and at temperatures above 100°, the autoclave is evacuated in order to dry it out, which results in a significant drop in pressure. If the pressure curve in the chamber of the autoclave is known, the sterilization detection device can, therefore, be pressure-activated and automatically allocate the sterilization status "sterile" to the sterile container after correct performance of a sterilization process. Furthermore, a pressure-activatable sterilization status detection device may also be used in other sterilization processes, for example, in gas plasma sterilization. Temperature-activated systems, however, function only in steam sterilization.

To improve the handling of the sterile container, it is advantageous for it to comprise a lower container part and an upper container part for closing the lower container part in a closed position of the sterile container. The lower container part may, in particular, be of tub-shaped construction. The upper container part may be in the form of a lid. Optional gas exchange openings of the sterile container may be selectively provided on the lower container part and/or on the upper container part and be temporarily or permanently opened by valves and/or germ barriers, for example, filters.

Depending on shape, size and intended use of the sterile container, it may be expedient for the sterilization status detection device to be arranged or formed on the lower container part and/or on the upper container part. In particular, it is conceivable to construct the sterilization status detection device in two or more parts, with one part thereof arranged or formed on the lower container part and another part thereof on the upper container part, so that they can only interact as sterilization status detection device when the upper container part closes the associated lower container part in the closed position.

It is expedient for the sterilization status detection device to be arranged or formed in the container interior or on the outside of the sterile container. The sterilization status detection device may be arranged or formed, in particular, in a protected manner, in or on the container interior. Arrangement thereof on the outside of the sterile container enables, in particular, interaction thereof in a simple way with an indication device or a closure device of the sterile container.

The sterilization status detection device is preferably configured for detecting a pressure gradient in the container interior or in the environment of the sterile container. Detecting a pressure gradient offers the advantage of being able to optimally coordinate a responding or a functioning of the sterilization status detection device with a conventional sterilization process in an autoclave. Several changes in pressure normally take place in a sterilization process. In particular, in relation to natural pressure fluctuations, for example, weather-dependent pressure fluctuations, these generate significantly larger pressure gradients, and so correct performance of a sterilization process can be determined in the best possible way by a sterilization status detection device for detecting a pressure gradient.

It is advantageous for the sterilization status detection device to comprise a piston-cylinder assembly. The piston-cylinder assembly makes it possible to convert pressure changes into a movement of the piston in order, for example, to activate an indication or lock a closure device. Alternatively, it is, of course, also conceivable for the sterilization status detection device to comprise any other kind of electrical or electromechanical pressure measuring device. However, a fully mechanized piston-cylinder assembly has the advantage over electrical pressure sensors that electric power is not required to operate it, and so provision of a piston-cylinder assembly allows batteries or a mains-dependent power supply to be dispensed with altogether.

To enable a pressure difference to be converted into a movement of the piston, it is expedient for the piston-cylinder assembly to comprise a double-acting cylinder. In a double-acting cylinder, two areas of the cylinder are normally separated from each other spatially by the piston. These are each provided with a connection, so that when different pressures are applied to the two connections, the piston is movable in a desired manner in one or the other direction.

In accordance with a further preferred embodiment of the invention, it may be advantageous for the cylinder to comprise a piston carrying a piston rod, and at least one reset member for moving the piston into a basic position. In this way, it can be ensured that before commencement of the sterilization process, the piston-cylinder assembly assumes a defined position, namely that in which the piston assumes the basic position.

It is advantageous for the piston rod to be movable further out of the cylinder or into the latter counter to the action of the at least one reset member. With the reset member, which, for example, may take the form of a spring element, for example, a helical spring, it is, in particular, possible to individually set which of the pressure relationships prevailing in the autoclave are able to bring about a movement of the piston at all. In this way, it is possible to set, in particular, purely mechanically, limit values of pressure gradients, which are to be reliably determined by the sterilization status detection device.

It is expedient for the at least one reset member to be a compression member and to be supported on a first piston side of the piston, which carries the piston rod. It is, for example, thus possible for the piston to be moved further out of the cylinder counter to the action of the reset member. This may, in particular, be a spring element in the form of a leaf or helical spring.

Alternatively, it is also conceivable for the at least one reset member to be a tension member and to be supported on a second piston side of the piston, which faces away from the piston rod.

It is advantageous for the cylinder to be divided by the piston into a first and a second cylinder space, and for the cylinder to comprise two connections which are each in fluid connection with one of the two cylinder spaces. As previously mentioned, in dependence upon the sterilization process, different pressures may prevail at the connections and act upon the piston, so that the latter can be moved in one or the other direction as a result of a change in pressure.

To enable pressure gradients to be easily detected, it is expedient for the two connections to have different opening cross sections. Different opening cross sections make it possible for a fluid, in particular, a gas to flow into and out of the respective cylinder space at different rates. In other words, the connection with the larger opening cross section can fill up quicker with the fluid or drain quicker if both connections are connected to the same environment, namely the interior of the autoclave. A change in pressure in the autoclave, i.e., a corresponding pressure gradient, then automatically results in a movement of the piston in one or the other direction. The different flow-in or flow-out times result at least temporarily in a pressure difference between the two cylinder spaces, which, in particular, may be used to move the piston.

The opening cross sections of the two connections expediently have a cross-sectional ratio of at least 2:1, preferably at least 4:1. To achieve a defined movement of the piston in dependence upon a pressure gradient in the autoclave, the opening cross sections and the reset member may be appropriately matched and coordinated.

In accordance with a further preferred embodiment of the invention, the sterile container may comprise an indication device coupled to the sterilization status detection device for automatically indicating the sterilization status of the sterile container. In particular, the indication device may be configured so as to change its color or indicate the sterilization status in the form of letters, numbers or words. It would also be conceivable to use an electronic indication device without mechanical parts, for example, an LCD or LED display.

The indication device can be constructed in a particularly simple way if it comprises at least one movable or actuatable indication member which is coupled to the piston rod. As a result of movement of the piston and the piston rod arranged thereon, the indication member can thus be moved in order to indicate to a user of the sterile container as a result of a change in position of the indication member whether the sterilization status of the sterile container is "sterile" or "unsterile". An indication device of purely mechanical construction has the advantage over an electronic one that electric power is not required for indicating the sterilization status and, in addition, corrosion problems with the hot steam sterilization can be avoided. If the indication member and the piston rod are immovably coupled to each other or are integrally constructed, it is, in principle, sufficient to provide only one reset member. If the indication member and the piston rod are movably coupled, it may, in particular, be provided that the indication member can only be pushed, but not pulled, with the piston rod. In this case, it is expedient to provide two reset members, one for the piston rod and one for the indication member.

It is expedient for the sterile container to comprise a closure device coupled to the sterilization status detection device for closing the sterile container. The closure device may, in particular, be constructed and/or arranged such that on opening the sterile container, for example, an indication device, without performance of a further sterilization process, irreversibly changes over from the status indication "sterile" to the status indication "unsterile". What may happen with purely temperature-activated sterilization status detection devices, namely that as a result of a rise in temperature and without the action of hot steam, an indication device may also indicate the sterilization state "sterile" again after opening of the sterile container, can thereby be prevented. Temperature changes have practically no influence on the pressure-activated sterilization status detection device in terms of occurrence of a minimum value of a pressure gradient required for detection of a completed sterilization process.

The sterile container can be closed and kept in the closed position in a simple and secure way if the closure device comprises a closure flap which is held movably on the upper container part or on the lower container part and in a closed position is able to be brought into engagement with a closure member on the respective other container part when the sterile container assumes the closed position. The closure flap can be held or mounted, in particular, pivotably and/or slideably on a part of the sterile container. In particular, the closure flap can be coupled to the indication device in such a way that upon transferring the closure flap from the closed position to a position in which the upper container part can be separated from the lower container part, the indication device automatically changes the sterilization status from "sterile" to "unsterile", in order to avoid any risk of the contents of the sterile container becoming unsterile without users of the sterile container gaining knowledge thereof.

It is expedient for the sterile container to comprise a locking device coupled to the sterilization status detection device for automatically locking the closure device, and for the locking device to comprise at least one locking member which is actuatable by the sterilization status detection device once the sterilization status "sterile" is reached, in order to secure the closure device in the closed position.

The sterile container can be constructed in a particularly simple and compact manner if the sterilization status detection device is arranged or formed on or in the closure flap. In particular, a movement of the closure flap can thus be used to open the sterile container in a simple way, for example, in order to automatically change the sterilization status indicated by an indication device, i.e., in particular, from "sterile" to "unsterile".

Furthermore, it is advantageous for the indication device to comprise a first holding device which holds the indication member in a position indicating the sterilization status sterile until the closure device of the sterile container is actuated in order to open the latter. In other words, the holding device is constructed such that when the sterilization status changes from "unsterile" to "sterile", it is automatically brought into a holding position and holds the indication member in the position indicating the sterilization status "sterile" until the holding device, as a result of movement or actuation of the closure device, for example, the closure flap, releases the indication member again, so that the indication device indicates the sterilization status "unsterile" again.

The first holding device is particularly simple to construct if it comprises at least one first holding member which holds the piston automatically in the position indicating the sterilization status "sterile".

Furthermore, it may be expedient for the at least one first holding member to be deflectable from a first holding member retention position to a first holding member release position as a result of movement of the piston and to be automatically moved into the first holding member retention position again after the position of the piston indicating the sterilization status "sterile" has been reached. In the holding member retention position, the first holding member can, for example, hold the deflected piston or the indication member held thereon in the position indicating the sterilization status "sterile".

In order that the first holding member can be easily brought from the holding member release position into the holding member retention position again, it is advantageous for the at least one first holding member to be deflectable from the first holding member retention position to the first holding member release position counter to the action of a first holding member reset member. The first holding member reset member may, in particular, take the form of a spring element, for example, a helical spring.

It is expedient for the locking device to comprise a second holding device which holds the at least one locking member in a position indicating the sterilization status until the closure device of the sterile container is actuated in order to open the latter. The closure device can, therefore, be held in a defined position by the second holding device.

The second holding device is particularly simple to construct if it comprises at least one second holding member which automatically holds the piston in the position indicating the sterilization status sterile.

The at least one second holding member is preferably deflectable from a second holding member retention position to a second holding member release position as a result of movement of the piston and is automatically moved into the second holding member retention position again after the position of the piston indicating the sterilization status "sterile" has been reached. The piston can thereby be easily held in a certain position. It thus forms, so to speak, a memory of the sterile container for owing to the second holding member it remains in its position allocated to the sterilization status "sterile", namely independently, in particular, of pressure or temperature changes in the environment of the sterile container.

In order to hold the at least one second holding member in a defined position, it is advantageous for it to be deflectable from the second holding member retention position to the second holding member release position counter to the action of a second holding member reset member. The second holding member reset member may also take the form of a spring element, for example, a helical spring.

The operation and the construction of the sterile container may be further simplified if the first and/or the second holding member comprise/comprises a slide surface for redirecting a force exerted by the piston in a piston movement direction on the first and/or the second holding member into a movement of the latter in a holding member movement direction. For example, a first or second holding member movable perpendicularly or substantially perpendicularly to the piston can thus be easily deflected as a result of movement of the piston.

The present invention further relates to a method for determining the sterilization status of a medical sterile container having a container interior for accommodating articles to be sterilized, wherein while the sterile container is undergoing a sterilization process in a sterilization apparatus, pressure differences to which the sterile container is thereby subjected are detected, and the sterilization status sterile is allocated to the sterile container if during the sterilization process a limit value for a pressure gradient per time unit is exceeded.

In particular, it may be expedient if it is a negative pressure gradient that is detected. Differently from purely temperature-monitored or temperature-activated determination of the sterilization status, the proposed method ensures that the sterilization status "sterile" is only allocated if sterilization has actually taken place. The pressure fluctuations or pressure gradients occurring in a hot steam sterilization process can thus be used as a clear indication that the sterilization process has been undergone properly.

A negative pressure gradient per time unit in a range of from −500 mbar/min to approximately −10 bar/min is preferably prescribed as limit value. For example, the range may be set so as to safely detect the unavoidable pressure drop in the autoclave after completion of the steaming stage, which occurs as a result of evacuation of the autoclave for drying out the sterile container.

It is advantageous if the pressure gradient is automatically determined by a pressure gradient measuring device during the sterilization process. This may be of mechanical or electronic or electromechanical construction. Operating errors by users can be avoided by the automatic determination of the pressure gradient.

The pressure gradient is preferably determined in the container interior or on the outside of the container during the sterilization process. In any case, it is advantageous to determine the pressure relationships in the interior of the sterilization apparatus.

In order to make it easy for a user of the sterile container and its contents to recognize whether the contents of the sterile container are sterile or unsterile, it is expedient for the sterilization status of the sterile container to be automatically indicated by an indication device.

In order to avoid, as far as possible, unintentional opening of the sterile container, it is advantageous if a closure device of the sterile container is automatically locked when the sterilization status "sterile" is reached. It is then only possible to open the sterile container in order to remove the sterile articles in it by specific unlocking.

Figure 1:
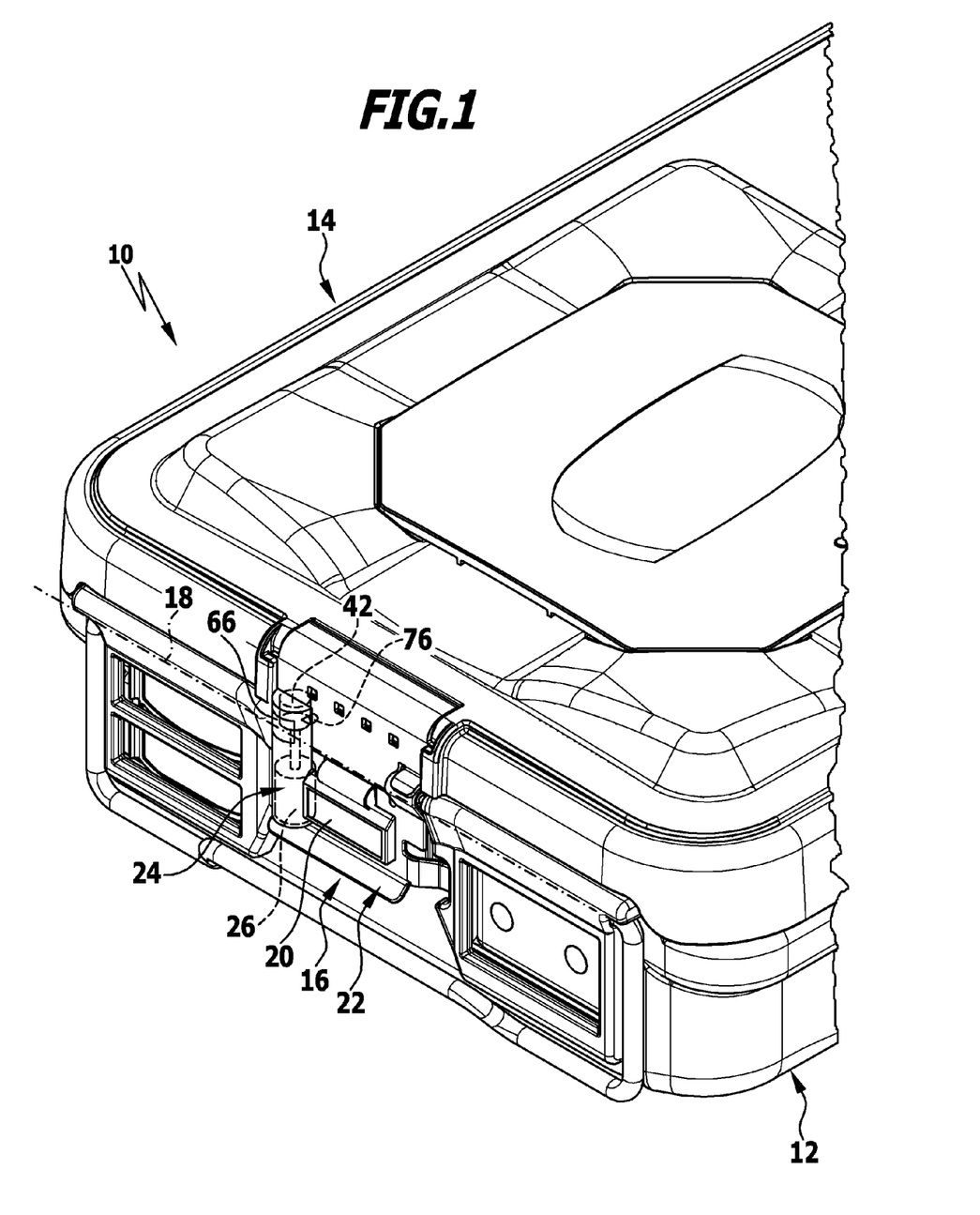
FIG. 1 shows a schematic, perspective partial view of a sterile container.

A sterile container denoted in its entirety by reference numeral 10, which comprises a tub-shaped lower container part 12 and an upper container part 14 for closing the lower container part 12 in a closed position of the sterile container 10, is shown schematically in FIG. 1. The sterile container also comprises a container interior, not specified in more detail, for accommodating articles to be sterilized. The construction of such a sterile container 10 is described, in particular, in DE 201 18 910 U1. The disclosure thereof is incorporated in its entirety in the present application.

The sterile container 10 may be provided on the lid or on the bottom with gas exchange openings, which are closed by germ barriers in the form of filter elements. This is also described in detail in DE 201 18 910 U1. As an alternative to filters, gas exchange openings may also take the form of inlet and/or outlet valves.

The sterile container 10 further comprises a closure device 16 for defined closure thereof. The closure device 16 comprises a closure flap 22 held for pivotal movement about a pivot axis 18 on the upper container part 14. Arranged or formed on the lower container part is a closure member 20 which, in a closed position, is in engagement, preferably in a clamping or latching manner, with the closure flap 22. However, the closed position can only be assumed when the sterile container 10 assumes the closed position, i.e., as shown in FIG. 1, the upper container part 14 closes the lower container part 12.

As described at the outset, the sterile container 10 is closed after it has been loaded with the articles to be sterilized, i.e., it assumes the closed position shown schematically in FIG. 1, and it is then placed with the contents in the autoclave. The closure device 16 is then in the closed position.

To be able to indicate unmistakably to a user of the sterile container 10 whether the sterile container 10 with its contents has undergone a sterilization process properly or not, the sterile container 10 comprises a pressure-activatable sterilization status detection device, denoted in its entirety by reference numeral 24, for detecting a sterilization status of the sterile container 10. In the embodiment shown in the Figures, this is arranged schematically on the outside of the upper container part 14, more specifically, on the closure flap 22. It is, however, also conceivable to arrange or form the sterilization status detection device 24 on the lower container part 12 or in the container interior.

The sterilization status detection device 24 is configured to detect a pressure gradient in the container interior or in an environment of the sterile container 10. For detection of a pressure gradient, the sterilization status detection device 24 comprises a piston-cylinder assembly 26 with a double-acting cylinder 28. A piston 30 or a piston disc is displaceably mounted in the conventional manner in the cylinder 28. The piston 30 carries on a first piston side 32 a piston rod 34 protruding perpendicularly from the latter. The piston rod 34 passes through a through-opening 36 in an end wall 38 and carries a cylindrical indication member 42 at its end 40 facing away from the piston 30.

The piston 30 divides the cylinder 28 into a first cylinder space 44 and a second cylinder space 46, which, in dependence upon a position of the piston 30, have different volumes. A reset member 48 in the form of a helical spring surrounding the piston rod 34 is arranged in the first cylinder space 44. The helical spring is supported, on the one hand, on the end wall 38 and, on the other hand, on the first piston side 32 of the piston 30. The reset member 48 takes the form of a compression member. Alternatively, the reset member could also take the form of a tension member, not shown, which is held, on the one hand, on a second piston side 52 facing away from the piston rod 30 and, on the other hand, on the end wall 54 located opposite the end wall 38.

The cylinder 28 further comprises two connections 56 and 58, which establish a fluid connection between an environment of the sterile container 10 and a cylinder space 44 and 46, respectively. A diameter 60 of the connection 56 connected to the first cylinder space 44 is approximately twice as large as a diameter 62 of the connection 58 connected to the second cylinder space 46. This results in a value of about 4:1 for a cross-sectional ratio of the connections 56 and 58.

Coupled with the sterilization status detection device 24 is an indication device 64. This comprises the previously mentioned indication member 42, which is arranged at the end 40 of the piston rod 34. Furthermore, there is provided on the closure flap 22 a window 66 or some other kind of opening which enables one to recognize from the outside in which position the indication member 42 is located.

In order to automatically hold the indication member 42 in a position which is allocated to the sterilization status "unsterile" of the sterile container, a further reset member 68 is provided, which is supported, on the one hand, on an end face 70 of the indication member 42, the end face 70 facing away from the end wall 38, and, on the other hand, on a stop face 72 which faces in the direction towards the cylinder 28. The cylinder 28 defines a longitudinal axis 74, and the piston rod 34 is aligned coaxially with the longitudinal axis 74, as are the indication member 42 and the reset member 68.

Figure 2A:
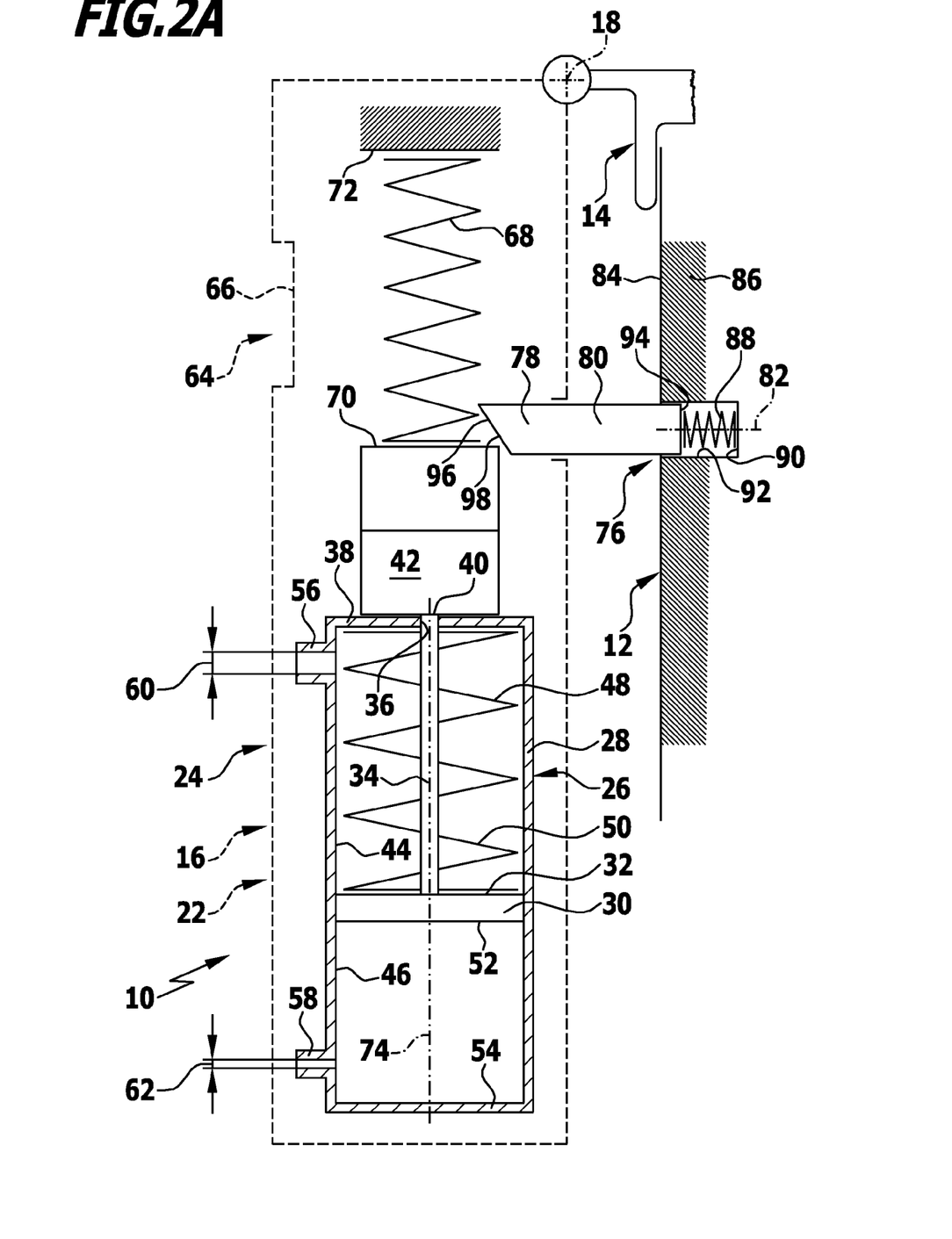
FIG. 2A shows a schematic representation of the principle underlying a sterilization status detection device in the "unsterile" position.
Figure 2B:
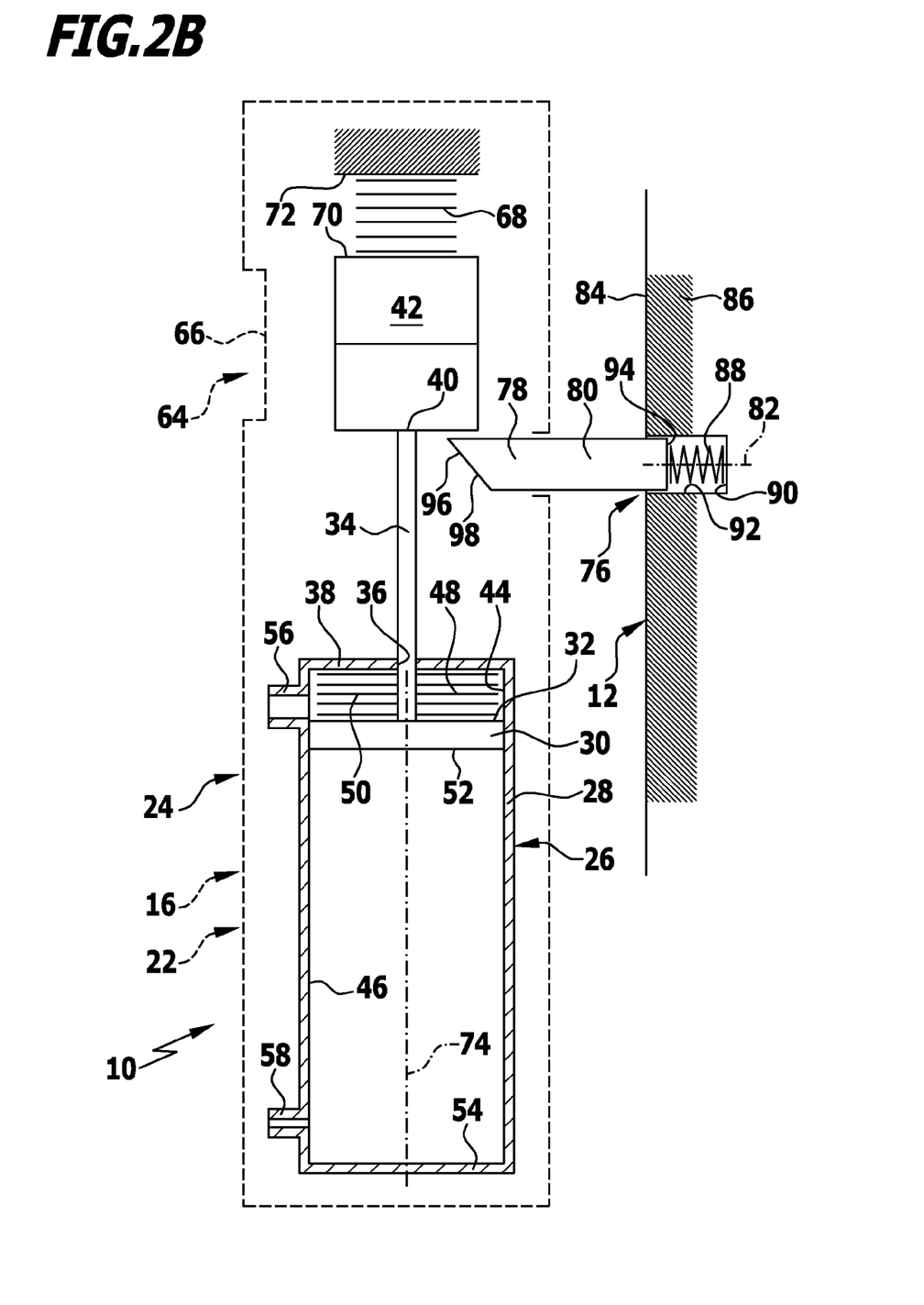
FIG. 2B shows a schematic representation of the assembly from FIG. 2A in the "sterile" sterilization status.

The sterile container 10 further comprises a holding device 76 which can hold the indication member 42 in a position indicating the sterilization status "sterile" until the closure device 16 of the sterile container 10 is actuated in order to open the latter. The holding device 76 comprises a holding member 78 which can automatically hold the piston 30 and the indication member 42 coupled to the latter in the position indicating the sterilization status "sterile". The holding member 78 takes the form of a cylindrical bolt 80, which defines a longitudinal axis 82 oriented perpendicularly to the longitudinal axis 74. The holding member 78 protrudes partially over a side wall 86 of the lower container part 12 facing away from the sterile container 10 and is held for displacement parallel to the longitudinal axis 82 relative to the lower container part 12. The holding member 78 is held in the side wall 86 of the lower container part 12 by a holding member reset member 88. In particular, this may take the form of a compression spring which is held, on the one hand, on the bottom 90 of a recess 92 formed in the side wall 86 of the lower container part 12 and, on the other hand, at the end 94 of the holding member 78 that faces the bottom 90. In this way, the holding member 78 can be moved counter to the action of the holding member reset member 88 in the direction towards the bottom 90. If force is not exerted on the holding member 78, the holding member reset member 88 forces the holding member 78 into its holding member restraint position shown schematically in FIGS. 2A and 2B, in which the end 94 is at the largest spacing from the bottom 90. A second end 96 of the holding member 78 that faces away from the end 94 defines a slide surface 98 inclined in relation to both the longitudinal axis 82 and the longitudinal axis 74. The slide surface 98 interacts with the indication member 42 in a manner described in more detail hereinbelow.

To be able to understand the way in which the pressure-activatable sterilization status detection device 24 operates, the curve of the pressure and the performance of the process over time in a typical sterilization process will first be described with reference to FIG. 3.

After loading the autoclave with the sterile container 10, the autoclave is evacuated in phase 1. This is followed by phase 2 in which the autoclave is subjected to steam for a short time. During this the pressure in the autoclave rises again to normal or atmospheric pressure $p_{atm}$. In phase 3 the autoclave is evacuated again in order to be subjected to hot steam again in phase 4. In phase 4, however, the pressure in the autoclave is raised to somewhat above the atmospheric pressure prevailing in the environment of the autoclave. In phase 5 the autoclave now under pressure above atmospheric with hot steam is evacuated again to atmospheric pressure. The actual hot steam sterilization takes place in phase 6 in which the sterilization chamber of the autoclave is subjected to hot steam, more specifically, up to the process temperature and up to the maximum process pressure $p_{max}$. The maximum process temperature and the maximum process pressure are then kept constant for a prescribed time, for example, 3 to 60 minutes. In phase 7 the sterilization chamber is evacuated again, more specifically, to far below normal pressure. The pressure below atmospheric is retained for a prescribed time in order to dry the container and its contents. Finally, the autoclave is ventilated again in phase 8. After the autoclave has cooled down, the sterile container can be removed at the end of phase 9.

Figure 3:
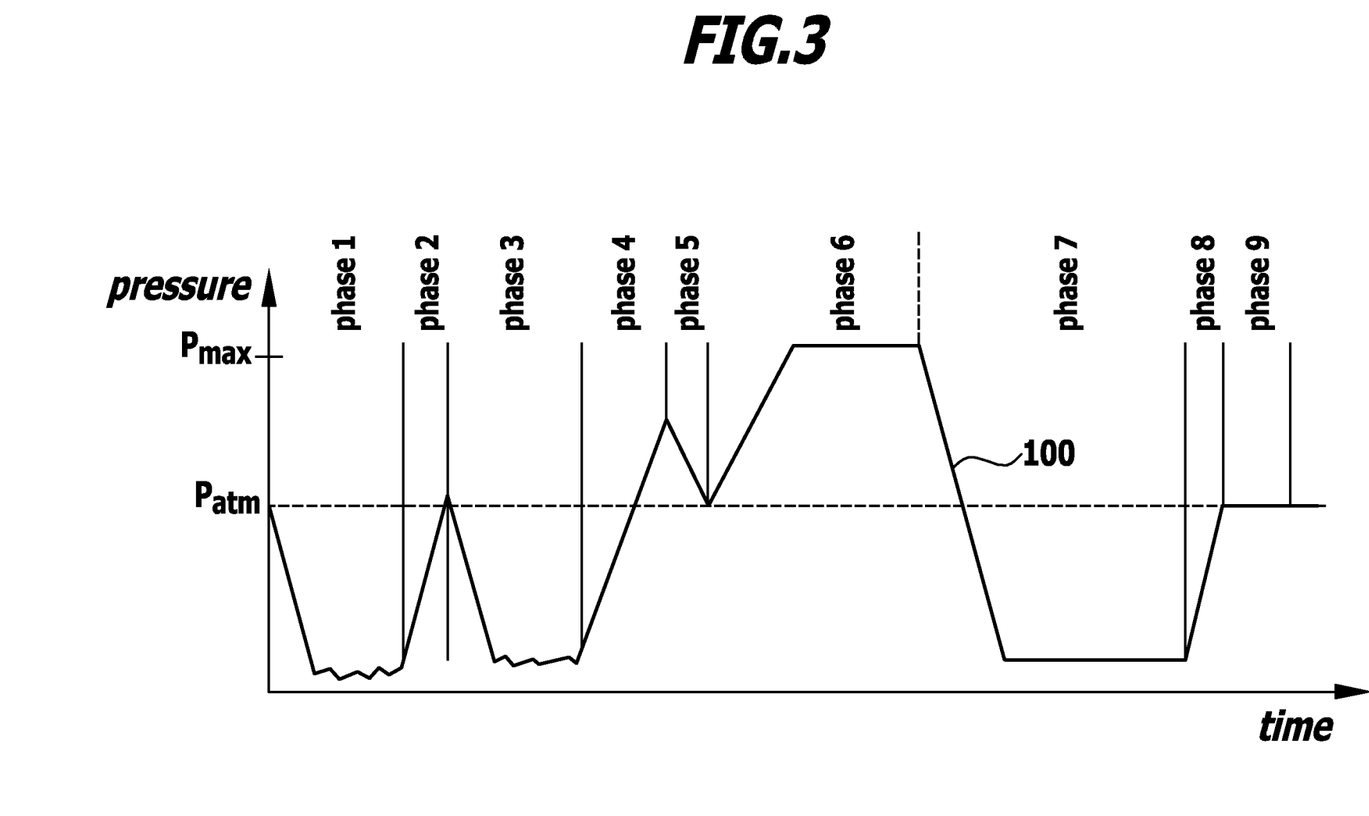
FIG. 3 shows a schematic representation of the pressure curve in the chamber of an autoclave during sterilization.

The diagram shown schematically in FIG. 3 indicates the pressure curve over time. However, the actual steam sterilization is already completed at the end of phase 6. Owing to the evacuation, a negative pressure gradient 100 occurs at the beginning of phase 7. The sterilization status detection device 24 is of such configuration that the pressure gradient 100 can be determined by it and, consequently, correct termination of phase 6 and proper performance of the sterilization process can be ascertained.

If the sterile container 10 is located in the sterilization chamber of the autoclave, the negative pressure gradient 100 results in the steam contained in the cylinder 28 escaping more quickly from the first cylinder space 44 than from the second cylinder space 46, namely owing to the different cross sections of the connections 56 and 58. The consequence of this is that, as shown schematically in FIG. 2B, the pressure in the second cylinder space 46 temporarily exceeds the pressure in the first cylinder space 44, with the result that the piston 30 is moved counter to the action of the reset member 48 in the direction towards the end wall 38. The piston rod 34 with the indication member 42 simultaneously moves in the direction towards the stop face 72. In doing so, the end face 70 slides on the slide surface 98 and pushes the holding member 78 counter to the action of the holding member reset member 88 in the direction towards the side wall 86 of the lower container part 12. Once the indication member 42 has passed the holding member 78 completely, the holding member 78, owing to the action of the compressed holding member reset member 88, is moved back again from the deflected position, referred to as holding member release position, into the holding member restraint position.

When the pressure difference between the two cylinder spaces 44 and 46 drops again, the piston 30 and the indication member 42 are moved back by the action of the reset member 48 and the reset member 68 in the direction towards the end wall 54, i.e., into the initial position. However, this is only possible until the indication member 42 strikes the holding member 78 assuming the holding member restraint position, as shown schematically in FIG. 2B. The indication member 42 is now located at the level of the window 66, so that an operator can recognize the indication member 42 from the outside through the window 66. If, for example, the indication member 42 is dyed a color, for example, red or green, it is then directly visible that after completion of the sterilization process the sterile container assumes the sterilization status "sterile".

If the closure device 16 is not actuated, i.e., the closure flap 22 is not pivoted from the closed position, the indication device 64 then remains unchanged. Together with the holding device 78 it forms, so to speak, a memory of the sterile container 10 and indicates its sterilization state.

If, however, the closure flap 22 is now opened, i.e., its free end is pivoted away from the side wall 86, the indication member 42 is then also pivoted away from the holding member 78, with the result that the latter can no longer hold back the indication member 42. The consequence is that the reset members 48 and 68 can move the piston 30 back into the basic position shown in FIG. 2A. However, the indication member 42 is also simultaneously moved in the direction towards the end wall 38, with the result that the indication member 42 is no longer visible through the window 66. It is, therefore, obvious to a user that the sterile container 10 has assumed the sterilization status "unsterile", i.e., sterility of the container contents is no longer guaranteed.

It is preferable for each closure flap 22 on the container to be equipped with the described sterilization status detection device 24.

If the indication device 64 shows the sterilization status "unsterile" then either the pressure gradient 100 during the sterilization process was insufficient to activate the sterilization status detection device 24 or the closure flaps 22 of the sterile container 10 have been tampered with.

Additionally or alternatively, a further holding device corresponding to the holding device 76 may be provided to lock the closure device 20 in the closed position. This increases the process reliability further.

In the method described hereinabove for determining the sterilization status of the sterile container 10, while the sterile container 10 is undergoing a sterilization process in a sterilization apparatus, at least relative pressure differences to which the sterile container 10 is subjected are detected, and the sterilization status "sterile" is automatically allocated to the sterile container 10 when a limit value for a pressure gradient per time unit, for example, the pressure gradient 100, is exceeded during the sterilization process. A negative pressure gradient per time unit in a range of from approximately –... Pa/s to approximately –... Pa/s is preferably prescribed as limit value. This is automatically determined with the sterilization status detection device during the sterilization process by a pressure gradient measuring device, for example, the piston-cylinder assembly 26. The pressure gradient can be determined in the container interior or on the outside of the sterile container 10 during the sterilization process. The sterilization status of the sterile container 10 is automatically indicated in the described manner by an indication device 64. Optionally, the closure device 16 of the sterile container 10 can be automatically locked when the sterilization status sterile is reached.

The invention claimed is:

1. Medical sterile container, comprising:
a container interior for accommodating articles to be sterilized,
a pressure-activatable sterilization status detection device for detecting a sterilization status of the sterile container, the sterilization status detection device comprising a piston-cylinder assembly, and
an indication device coupled to the sterilization status detection device for automatically indicating the sterilization status of the sterile container, the indication device comprising at least one movable or actuatable indication member which is coupled to a piston rod of the piston-cylinder assembly.

2. Medical sterile container in accordance with claim 1, further comprising a lower container part and an upper container part for closing the lower container part in a closed position of the sterile container.

3. Medical sterile container in accordance with claim 1, wherein the sterilization status detection device is arranged or formed in the container interior or on an outside of the sterile container.

4. Medical sterile container in accordance with claim 1, wherein the sterilization status detection device is configured for detecting a pressure gradient in the container interior or in an environment of the sterile container.

5. Medical sterile container in accordance with claim 1, wherein the piston-cylinder assembly comprises a double-acting cylinder.

6. Medical sterile container in accordance with claim 5, wherein the piston-cylinder assembly comprises a piston carrying the piston rod, and at least one reset member for moving the piston into a basic position.

7. Medical sterile container in accordance with claim 6, wherein the piston rod is movable further out of the cylinder or into the cylinder counter to an action of the at least one reset member.

8. Medical sterile container in accordance with claim 6, wherein the at least one reset member is one of a compression member which is supported on a first piston side of the piston, which carries the piston rod, and a tension member which is supported on a second piston side of the piston, which faces away from the piston rod.

9. Medical sterile container in accordance with claim 6, wherein the cylinder is divided by the piston into a first and a second cylinder space, and the cylinder comprises two connections which are each in fluid connection with one of the first and the second cylinder spaces.

10. Medical sterile container in accordance with claim 9, wherein the two connections have different opening cross sections.

11. Medical sterile container in accordance with claim 10, wherein the opening cross sections of the two connections have a cross-sectional ratio of at least 2:1.

12. Medical sterile container in accordance with claim 1, further comprising a closure device coupled to the sterilization status detection device for closing the sterile container.

13. Medical sterile container in accordance with claim 12, further comprising a locking device coupled to the sterilization status detection device for automatically locking the closure device, and the locking device comprising at least one locking member which is actuatable by the sterilization status detection device once the sterilization status of sterile is reached, in order to secure the closure device in the closed position.

14. Medical sterile container in accordance with claim 1, wherein the indication device comprises a first holding device which holds the indication member in a position indicating the sterilization status of sterile until the closure device of the sterile container is actuated in order to open the sterile container.

15. Medical sterile container in accordance with claim 14, wherein the first holding device comprises at least one first holding member which holds the piston automatically in the position indicating the sterilization status of sterile.

16. Medical sterile container in accordance with claim 15, wherein the at least one first holding member is deflectable from a first holding member retention position to a first holding member release position as a result of movement of the piston and is automatically moved into the first holding member retention position again after the position of the piston indicating the sterilization status of sterile has been reached.

17. Medical sterile container in accordance with claim 13, wherein the locking device further comprises a second holding device which holds the at least one locking member in a position indicating the sterilization status until the closure device of the sterile container is actuated in order to open the sterile container.

18. Medical sterile container in accordance with claim 17, wherein:
    the piston-cylinder assembly comprises a double-acting cylinder and a piston,
    the second holding device comprises at least one second holding member which automatically holds the piston in the position indicating the sterilization status of sterile.

19. Medical sterile container in accordance with claim 15, further comprising:
    a closure device coupled to the sterilization status detection device for closing the sterile container,
    a locking device coupled to the sterilization status detection device for automatically locking the closure device, the locking device comprising:
        at least one locking member which is actuatable by the sterilization status detection device once the sterilization status of sterile is reached, in order to secure the closure device in the closed position, and
        a second holding device which holds the at least one locking member in a position indicating the sterilization status until the closure device of the sterile container is actuated in order to open the sterile container,
    wherein at least one of the first and the second holding members comprises a slide surface for redirecting a force exerted by the piston in a piston movement direction on the at least one of the first and the second holding members into a movement of the at least one of the first and the second holding members in a holding member movement direction.

20. Method for determining the sterilization status of a medical sterile container having a container interior for accommodating articles to be sterilized, comprising:
    while the sterile container is undergoing a sterilization process in a sterilization apparatus, detecting pressure differences to which the sterile container is thereby subjected, and
    allocating a sterilization status of sterile to the sterile container once a limit value for a pressure gradient per time unit is exceeded during the sterilization process.

21. Method in accordance with claim 20, wherein a negative pressure gradient per time unit in a range of from approximately −500 mbar/min to approximately −10 bar/min is prescribed as the limit value.

22. Method in accordance with claim 20, wherein a closure device of the sterile container is automatically locked when the sterilization status of sterile is reached.

23. Medical sterile container in accordance with claim 10, wherein opening cross sections of the two connections have a cross-sectional ratio of at least 4:1.

* * * * *